US00PP13605P2

(12) United States Plant Patent
Stroet

(10) Patent No.: US PP13,605 P2
(45) Date of Patent: Feb. 25, 2003

(54) PORTULACA PLANT NAMED 'CINDY'

(76) Inventor: Theodorus B. J. Stroet, Wagenaarstraat 24, 2671 TZ Naaldwijk (NL)

( * ) Notice: Subject to any disclaimer, the term of this patent is extended or adjusted under 35 U.S.C. 154(b) by 0 days.

(21) Appl. No.: 10/016,877

(22) Filed: Dec. 14, 2001

(51) Int. Cl.[7] ..... A01H 5/00
(52) U.S. Cl. ..... Plt./263

(58) Field of Search ..... Plt./263

*Primary Examiner*—Bruce R. Campell
*Assistant Examiner*—June Hwu
(74) *Attorney, Agent, or Firm*—C. A. Whealy

(57) ABSTRACT

A new and distinct cultivar of Portulaca plant named 'Cindy', characterized by its outwardly spreading and trailing plant habit; freely branching growth habit; relatively rapid growth rate; double flower form; and yellow and orange bi-colored flowers.

1 Drawing Sheet

BOTANICAL CLASSIFICATION/CULTIVAR DESIGNATION

*Portulaca grandiflora* cultivar Cindy.

BACKGROUND OF THE INVENTION

The present Invention relates to a new and distinct cultivar of Portulaca plant, botanically known as *Portulaca grandiflora*, and hereinafter referred to by the name 'Cindy'.

The new Portulaca is a product of a planned breeding program conducted by the Inventor in Naaldwijk, The Netherlands. The objective of the breeding program is to create new Portulacas with interesting flower forms and flower colors.

The new Portulaca is a naturally-occurring whole plant mutation of an unnamed selection of *Portulaca grandiflora*, not patented, that was discovered and selected by the Inventor during the summer of 1999 in a controlled environment in Naaldwijk, The Netherlands, on the basis of its yellow and orange bi-colored double flowers.

Asexual reproduction of the new cultivar by cuttings taken in a controlled environment in Naaldwijk, The Netherlands since 1999, has shown that the unique features of this new Portulaca are stable and reproduced true to type in successive generations.

SUMMARY OF THE INVENTION

Plants of the cultivar Cindy have not been observed under all possible environmental conditions. The phenotype may vary somewhat with variations in environment and culture such as temperature, light intensity, and daylength without, however, any variance in genotype.

The following traits have been repeatedly observed and are determined to be the unique characteristics of 'Cindy'. These characteristics in combination distinguish 'Cindy' as a new and distinct cultivar:

1. Outwardly spreading and trailing plant habit.
2. Freely branching growth habit, dense and full plants.
3. Relatively rapid growth rate.
4. Double flower form.
5. Yellow and orange bi-colored flowers.

In addition to flower coloration, plants of the new Portulaca differ from plants of the parent selection and other Portulaca cultivars known to the Inventor in the following characteristics:

1. Plants of the new Portulaca are not as compact as plants of the parent selection and other known cultivars of Portulaca.
2. Plants of the new Portulaca have a more rapid growth rate than plants of the parent selection and other known cultivars of Portulaca.
3. Plants of the new Portulaca have double flowers whereas plants of the parent selection and other known cultivars of Portulaca have single flowers.

Plants of the new Portulaca differ from plants of the cultivar Sleeping Beauty, U.S. Plant patent application Ser. No. 10/016,878 filed concurrently, and the cultivar Snow White, U.S. Plant patent application Ser. No. 10/016,879 filed concurrently, primarily in flower coloration.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Portulaca.

The photograph at the top of the sheet comprises a side perspective view of a typical flowering plant of 'Cindy'.

The photograph at the bottom of the sheet comprises a close-up view of a typical flowering plant of 'Cindy' showing the foliage and flowers.

DETAILED BOTANICAL DESCRIPTION

Plants used for the aforementioned photographs and following observations and measurements were planted into 15-cm containers and grown for about four months during the summer in a glass-covered greenhouse in Aalsmeer, The Netherlands. During the production of the plants, the day and night temperatures averaged 20° C.

In the following description, color references are made to The Royal Horticultural Society Colour Chart, Edition 1995, except where general terms of ordinary dictionary significance are used.

Botanical classification: *Portulaca grandiflora* cultivar Cindy.

Parentage: Naturally-occurring whole plant mutation of an unnamed selection of *Portulaca grandiflora*, not patented.

Propagation:

*Type.*—By cuttings.

*Time to initiate roots.*—About 12 days at 20° C.

*Root description.*—Fine, freely branching.

Plant description:

*Form.*—Outwardly spreading and trailing plant habit. Freely branching with lateral branches potentially developing at every node without pinching; dense and full plants.

*Growth rate.*—Relatively rapid; about eight weeks are required to produce a finished flowering plant in a 10-cm container.

*Plant height.*—About 18 cm.

*Plant diameter.*—About 32.5 cm.

*Lateral branches.*—Length: About 30 to 50 cm. Diameter: About 4 mm. Internode length: About 1.3 to 7.4 cm. Strength: Strong. Texture: Smooth, glabrous. Color: 146D, overlain with slight anthocyanin, 178A.

*Foliage description.*—Arrangement: Alternate, simple. Length: About 1.6 cm. Width: About 7 mm. Shape: Oblong to ovate. Apex: Rounded acute. Base: Obtuse. Margin: Entire. Texture: Smooth, glabrous; fleshy. Venation pattern: Pinnate. Petiole length: About 1.5 mm. Petiole diameter: About 1 mm. Color: Young foliage, upper surface: 137C. Young foliage, lower surface: 147B. Fully expanded foliage, upper surface: 144A. Fully expanded foliage, lower surface: 148B. Venation, upper and lower surfaces: Close to 147B. Petiole, upper and lower surfaces: 146D.

Flower description:

*Flower type and habit.*—Numerous double rotate flowers; solitary or in clusters. Flowers face upright or outward. Freely flowering with about 20 to 40 flowers and flower buds per lateral branch. Flowers not persistent.

*Time to flower.*—Early flowering, plants begin to flower about six weeks after planting.

*Natural flowering season.*—In the northern hemisphere, plants flower during the summer and autumn; flowering recurrent during this period.

*Flower longevity on the plant.*—About three days.

*Fragrance.*—None detected.

*Flowers.*—Diameter: About 2 cm. Depth (height): About 1.2 cm.

*Flower buds* (*before showing color*).—Length: About 5 mm. Diameter: About 3 mm. Shape: Roughly ovoid. Color: 143A.

*Corolla.*—Arrangement/appearance: Five petals in a single whorl, surrounding 30 to 40 petaloids which are transformed stamens and pistils. Petal length: About 1.3 cm. Petal width: About 7 mm. Petal shape: Obovate. Petal apex: Cuspidate. Petal base: Obtuse. Petal margin: Entire. Petal texture: Smooth, satiny. Petal color: When opening, upper surface: 9B. When opening, lower surface: 10C. Fully opened, upper surface: 7A. Fully opened, lower surface: 6C. Petaloid length: About 8 mm. Petaloid width: About 2.5 mm. Petaloid shape: Oblanceolate. Petaloid apex: Acute. Petaloid base: Attenuate. Petaloid margin: Entire. Petaloid texture: Smooth, satiny. Petaloid color, upper and lower surfaces: Towards apex: 14C. Mid-section: 31D. Towards base and along margin: 67B.

*Calyx.*—Appearance: Two-cleft. Length: About 5.5 mm. Diameter: About 3.5 mm. Shape: Deltoid. Apex: Acute. Base: Cuneate. Texture, upper and lower surfaces: Smooth, glabrous. Color, upper and lower surfaces: 145A.

*Peduncles.*—Length: About 2.5 mm. Diameter: About 1.5 mm. Strength: Strong. Angle: Mostly erect. Texture: Smooth, glabrous. Color: 144D.

*Reproductive organs.*—No stamens or pistils observed; reproductive organs transformed into petaloids.

*Seed/fruit.*—Seed nor fruit production has not been observed.

Disease/pest resistance: Plants of the new Portulaca have not been noted to be resistant to pathogens or pests common to Portulaca.

It is claimed:

1. A new and distinct cultivar of Portulaca plant named 'Cindy', as illustrated and described.

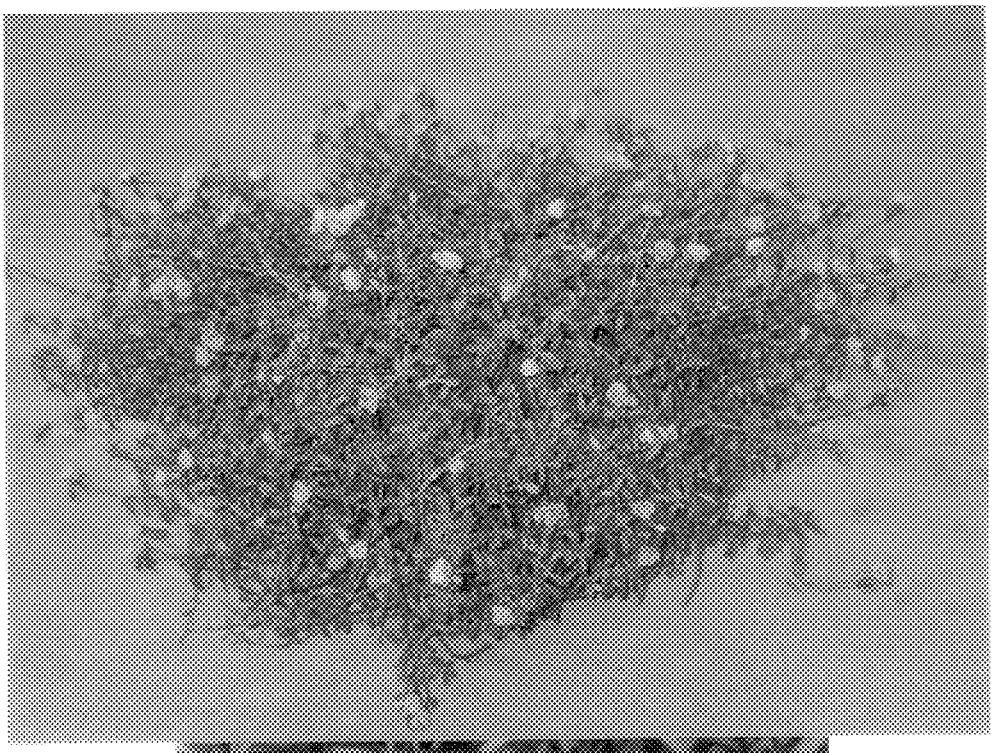
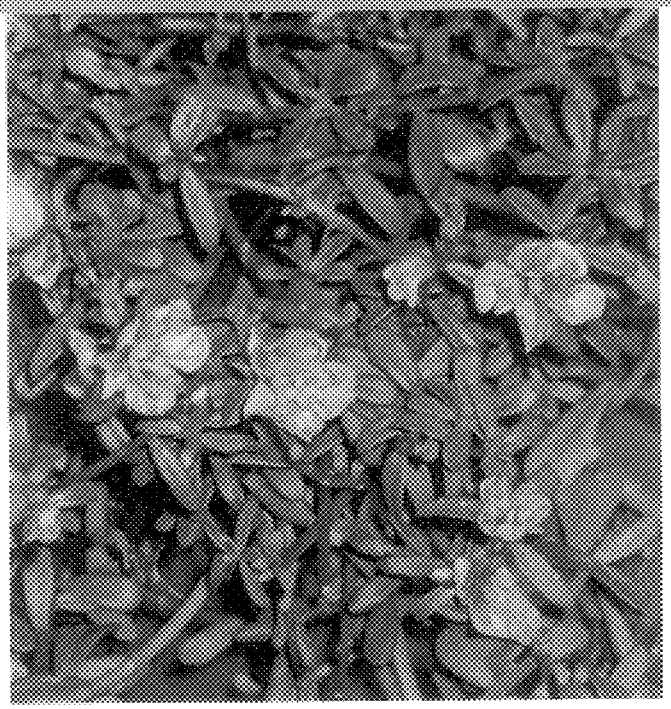

* * * * *